US012338560B2

(12) United States Patent
Harwood et al.

(10) Patent No.: US 12,338,560 B2
(45) Date of Patent: Jun. 24, 2025

(54) METHOD OF MAKING BESPOKE KNITTED COMPRESSION GARMENT

(71) Applicant: ADVANCED THERAPEUTIC MATERIALS LIMITED, Manchester (GB)

(72) Inventors: Adam Harwood, Manchester (GB); Clive Gunther, Manchester (GB); Najmal Hassan Chaudhury, Manchester (GB); James Sopper, Manchester (GB)

(73) Assignee: ADVANCED THERAPEUTIC MATERIALS LIMITED, Manchester (GB)

( * ) Notice: Subject to any disclaimer, the term of this patent is extended or adjusted under 35 U.S.C. 154(b) by 382 days.

(21) Appl. No.: 18/004,819

(22) PCT Filed: Jul. 9, 2021

(86) PCT No.: PCT/GB2021/051769
§ 371 (c)(1),
(2) Date: Jan. 9, 2023

(87) PCT Pub. No.: WO2022/008932
PCT Pub. Date: Jan. 13, 2022

(65) Prior Publication Data
US 2023/0250567 A1 Aug. 10, 2023

(30) Foreign Application Priority Data
Jul. 10, 2020 (GB) .................................... 2010687

(51) Int. Cl.
*D04B 15/66* (2006.01)
*A61F 13/00* (2024.01)
(Continued)

(52) U.S. Cl.
CPC ........ *D04B 15/66* (2013.01); *A61F 13/00987* (2013.01); *A61F 13/08* (2013.01);
(Continued)

(58) Field of Classification Search
CPC ..... D04B 15/66; D04B 1/24; A61F 13/00987; A61F 13/08; G05B 19/4155;
(Continued)

(56) References Cited

U.S. PATENT DOCUMENTS 11,872,149 B2 * 1/2024 Rodriguez ............ A61F 5/0109
12,024,802 B2 * 7/2024 Jayasundara .......... H05B 3/342
(Continued)

FOREIGN PATENT DOCUMENTS

| EP | 3528208 A1 | 8/2019 |
| EP | 3878351 A1 | 9/2021 |
| WO | 2005106087 A1 | 11/2005 |

OTHER PUBLICATIONS

Written Opinion of International Search Report in International Application No. PCT/GB2021/051769, mailed Dec. 22, 2021.
(Continued)

*Primary Examiner* — Allen H Nguyen
(74) *Attorney, Agent, or Firm* — Kim IP Law Group LLC

(57) ABSTRACT

A method of making a bespoke knitted compression garment. The method comprises providing a representation of a body part on which the compression garment is to be worn (S102), the representation comprising a plurality of datapoints. A desired pressure configuration to be applied by the compression garment on the body part is determined (S104). Representation courses around the representation are defined (S106). Sets of datapoints for each representation course are selected (S107). A curve for each set of datapoints and a circumference value of each curve is calculated (S108, S109). A pressure to be applied by each course is determined
(Continued)

(S111) and a material for knitting, and a number of needles for each representation course, is determined based on the course pressure of the associated material course, a strain characteristic of the material, and the circumference value of the associated curve (S112). A garment is knitted according to the number of needles and the material (S113, S114).

20 Claims, 9 Drawing Sheets

(51) Int. Cl.
*A61F 13/08* (2006.01)
*D04B 1/24* (2006.01)
*G05B 19/4155* (2006.01)
*A41D 13/12* (2006.01)

(52) U.S. Cl.
CPC ............ *D04B 1/24* (2013.01); *G05B 19/4155* (2013.01); *A41D 13/1236* (2013.01); *A41D 2500/10* (2013.01); *G05B 2219/45194* (2013.01)

(58) Field of Classification Search
CPC ...... G05B 2219/45194; A41D 13/1236; A41D 2500/10
USPC .......................................................... 382/111
See application file for complete search history.

(56) References Cited

U.S. PATENT DOCUMENTS

2020/0174453 A1 6/2020 Bertaux Hegemann
2022/0338577 A1* 10/2022 Eschen ................. D04B 37/02
2023/0399777 A1* 12/2023 Ng ........................ D04B 15/66

OTHER PUBLICATIONS

International Search Report in International Application No. PCT/GB2021/051769, mailed Dec. 22, 2021.
United Kingdom Search Report issued in counterpart United Kingdom Application No. GB2010687.8, mailed Jan. 4, 2021.
Preliminary Search Report in International Application No. PCT/GB2021/051769, mailed, Jan. 19, 2021.

* cited by examiner

METHOD OF MAKING BESPOKE KNITTED COMPRESSION GARMENT

CROSS-REFERENCE TO RELATED APPLICATION(S)

This is a national stage application filed under 35 U.S.C. § 371 based on International Patent Application No. PCT/GB2021/051769, filed Jul. 9, 2021, which claims priority to United Kingdom Patent Application No. GB2010687.8, filed Jul. 10, 2020, the disclosures of which are incorporated herein by reference in their entireties.

The present invention relates to a method of making a compression garment, in particular to a method of making a bespoke knitted compression garment. The invention further relates to a knitted-compression-garment manufacturing system, a knitted compression garment, a method of modelling a bespoke compression garment, and a method of providing a matched compression garment to a patient.

Compression garments are worn on a person's or patient's body part and apply pressure to the body part to improve blood circulation therein. This can help to improve or cure a number of different health conditions. Compression garments may be commonly worn on limbs, for example on the leg and/or foot. Compression garments worn on the leg and/or foot may be termed compression stockings or compression socks.

Compression garments are conventionally knitted. Knitting, rather than weaving, may be used for compression garments since knitting is suited to cylindrical garments and compression garments are typically cylindrical. As such, knitted compression garments are quicker and more cost effective to manufacture than woven garments and may provide greater comfort than woven garments.

A knitted compression garment may typically comprise a plurality of courses or bands of material. These have a circumference which, when at rest, is smaller than a circumference of the associated body part. As such, the courses are required to be strained to be worn over the body part, which would cause a pressure to be applied on the body part.

It is important that the compression garment provided to the patient is configured to accurately apply a clinically predetermined pressure. If the pressure which is applied is too great, then this can cause pain or discomfort. If the pressure is too little, then the patient's blood circulation may not be improved.

Furthermore, some patients may struggle to put on compression garments. This is since the compression garment requires straining to allow the garment to be put on. It would therefore be desirable to ensure that the garment may be convenient to be put on.

Bespoke compression garments are known, and these can assist with accurately applying the predetermined pressure. However, improving the designing and manufacturing method of bespoke compression garments is desirable to improve an accuracy of the pressure applied by the garment. Additionally, it is desirable to reduce or eliminate a human involvement with the method to increase a speed of design or manufacture of the garment.

The present invention seeks to provide a solution to these problems.

According to a first aspect of the present invention, there is provided a method of making a bespoke knitted compression garment comprising material courses, the method comprising the steps of: a) providing a representation of a body part on which the compression garment is to be worn, the representation comprising a plurality of datapoints; b) determining a pressure configuration to be applied by the compression garment on the body part; c) defining a plurality of representation courses around the representation, each representation course representing one of the material courses of the compression garment when worn on the body part; d) selecting, for each representation course, a set of datapoints from the plurality of datapoints, each set of datapoints being located within one of the representation courses; e) fitting a curve to each set of datapoints; f) calculating a circumference value of each curve; g) determining a course pressure to be applied by each material course based on the pressure configuration; h) selecting a material for knitting at least part of the compression garment and determining a number of needles for each representation course based on the course pressure of the associated material course, a strain characteristic of the material, and the circumference value of the associated curve; i) producing a knitting pattern based on the number of needles for each representation course; and j) knitting the compression garment based on the or each knitting pattern using said material.

The above method allows for compression garments to be produced, preferably at least in part automatically, which would accurately apply a clinically predetermined pressure to the body part. The compression garment would be individual to the patient. Calculating a curve which is based on the actual data points recorded in the scan provides an accurate circumference value of the course. This is opposed to calculating a curve, such as a spline, convex hull or other fitting curve, based on boundary curves or other approximations of the data. This ensures that the number of needles or wales, which defines the unstrained circumference of the course, can be accurately determined, and therefore that the course will accurately apply a required pressure.

Preferably, said pressure configuration may be non-uniform and at least two of the course pressures are different to each other. A non-uniform pressure configuration, such as a graduated pressure, may be clinically advantageous for a patient.

Advantageously, at least one representation course may be non-planar. Courses of the garment when worn on a curved or non-linear portion of the body adopt a curved or non-planar form. It will be appreciated that a curved course will have a greater circumference than an equivalent non-curved course. As such, to more accurately model and calculate the circumference which the course will adopt, it is advantageous to model the representation course as non-planar.

Beneficially, the or each non-planar representation course may be defined as having at least two planar portions at an angle to each other. This simplifies calculation of the circumference of the representation, as opposed to modelling a curved course, whilst still accounting for at least part of the increase in circumference associated with a curved course.

In a preferable embodiment, during step e) said two planar portions of the or each non-planar representation may be transformed so as to be coplanar. This simplifies calculation of the curve, as opposed to modelling a non-planar curve.

Additionally, the representation courses may each have at least one course height, the or each non-planar representation course having a non-uniform course height. A non-uniform course height allows for the representation courses to accurately reflect the garment as worn, and so can prevent bunching of the garment when worn.

Optionally, the representation courses may each have at least one course height, representation courses having a greater circumference value having a lower course height. An accurate number of courses can be defined to provide a garment of a correct height. This is since courses which are more strained may have a lower course height.

Preferably, the method may further comprise the step k) after step e) and prior to step h) of defining a plurality of reference points around the circumference of each curve and determining a radius of curvature value of the curve at each reference point, and during step h) the material and number of needles of each representation course is based on the radius of curvature of the reference points of the associated curve. The pressure applied by a course depends on the radius of curvature of the course. Since the radius of curvature of a leg may vary around a given circumference of the leg, to avoid or limit unacceptable high local levels of pressure, it is advantageous to accurately determine the radius of curvature at different locations around the curve.

Advantageously, the representation of the body part may include both at least a majority of a lower leg and at least a majority of a foot. This allows for a stocking to be automatically modelled and manufactured which is bespoke to both the leg and a foot of a patient.

Beneficially, the method may further comprise the step l) prior to step c) of analysing the representation to determine whether material courses of a first area of the garment when worn will be angularly offset relative to material courses of a second area of the garment when worn. As such, a single representation can be used and courses accurately defined for the two areas automatically despite their offset, without requiring human involvement to determine the location of offset areas.

In a preferable embodiment, during step l) the first area may comprise the lower leg and the second area may comprise the foot.

Optionally, during step l) said analysing may comprise determining at least one transition point which characterises a transition between leg and foot, forwardmost and/or rearwardmost datapoints of the representation defining a curve or respective curves, the or each transition point being found by determining a point of maximum change in gradient of said curve.

Additionally, during step l) before identifying the or each transition point, a selection of the forwardmost and/or rearwardmost datapoints of the representation may be made based on typical transition point characteristics. This allows for the transition point to be accurately determined. In other words, erroneous locations of the transition point based on local curves far from the transition between body part areas may be avoided.

Preferably, during step l) said analysing comprises determining at least one transition point which characterises a transition between leg and foot on a forwardmost surface, said transition point being determined by the smallest distance on said forwardmost surface to a point which defines a back of a heel or a transition point between leg and foot on a rearwardmost surface. The transition point on the forwardmost surface may otherwise be defined as the transition point on the anterior surface or foot dorsum, or the anterior foot/tibia transition point. To find the transition point on the forwardmost surface in this way, a point which defines a back of a heel may first need to be found. This may be done via determining a point of maximum change in gradient of the curve on the rearwardmost surface. However, other means, such as manual selection, may be considered.

Defining the transition point on the forwardmost surface by using the back of the heel, rather than by using the gradient of the forwardmost surface, has been found to be more reliable and less open to abnormalities, especially when performed on patients with oedema.

Beneficially, the curve may extend through each datapoint of one set.

Preferably, the method may further comprise the step m) prior to step a) of scanning said body part to produce said representation and analysing said representation to determine errors of said representation.

Additionally, during step m) said errors may be automatically corrected and/or an alert is provided to instruct repetition of the scanning. If the errors are sufficiently small and can be corrected, then this prevents or limits the requirement for another scan to be taken. If the errors cannot be corrected, then an alert allows for the clinician to be notified that another scan is required, before the patient leaves the clinic.

Preferably, the representation in step a) may be provided with reference to a three-dimensional Cartesian coordinate system, said representation may be a misoriented representation having an incorrect angle relative to a z-axis of said coordinate system, and the method may further comprise a step n) after step a) wherein said misoriented representation may be transformed to said representation having a correct orientation relative to said z-axis via rotating said misoriented representation by an angle defined between two markers having different z-axis positions, each marker may be defined by an average x-axis or y-axis position of respective groups of datapoints of the misoriented representation having the same z-axis position. This allows for the scan to be taken with the patient's body part in an orientation which is not representative of the body part when conventionally positioned. This may allow for the scan to be conveniently performed.

Advantageously, during step i) said knitting pattern may be smoothed to generate a smoothed knitting pattern to prevent or limit dropped stitches during step j).

Beneficially, the knitting pattern may be smoothed via adjusting the number of needles of the representation courses so that each knitting course of the smoothed knitting pattern has at least four adjacent knitting courses having an equal value of needles.

Additionally, the knitting courses may be aligned with respect to an internal line through the knitting pattern so that the garment when knitted is shaped at forwardmost and rearwardmost surfaces. Shaping of the garment at forwardmost and rearwardmost surfaces, or around the entirety of the circumference, of at least a portion of the garment is representative for the upper leg and for patients with conditions such as oedema, obesity or lipoedema.

Preferably, the material courses are flat knitted.

Optionally, the curve may be a spline so that step e) comprises: calculating a spline for each set of data points.

Additionally or alternatively, the curve may be a convex hull so that step e) comprises: calculating a convex hull for each set of data points. A convex hull is the smallest convex set or convex shape which contains all the data points of the set. It is analogous to a rubber band being stretched across the data points of the set. As such, points in the interior of the convex hull are effectively ignored when drawing the curve, since taking these points into account would mean the curve would not be convex.

Since the course of a compression garment can be considered to be like a rubber band, the curve having the property of a convex hull is a suitable modelling technique for accurately representing the garment on the user. As such, using a convex hull allows for a more accurate calculation of the circumference of the course, and thus a more accurate calculation of pressure and strain. Areas of the body which lie within a concavity and therefore will not have any pressure applied by the garment can also be identified by using a convex hull. The ankle has such areas.

The use of the convex hull also improves the reliability of the process since erroneous data lying inside the convex hull can be routinely ignored.

If a spline is calculated to fit a curve to the datapoints of the set, then preferably the spline is a convex hull.

Preferably, the method according to the first aspect to the invention is partly computer implemented. For example, steps a) to i) and k) to n) are computer implemented.

According to a second aspect of the invention there is provided a knitted-compression-garment manufacturing system for the method as claimed in any one of the preceding claims comprising: a body part scanner for providing a representation of a body part on which the compression garment is to be worn, the representation comprising a plurality of datapoints; pressure configuration data representing a pressure to be applied by the compression garment on the body part; material data including strain characteristics of at least one material; a processor configured to define a plurality of representation courses around the representation, each representation course representing one of the material courses of the compression garment when worn on the body part; select, for each representation course, a set of datapoints from the plurality of datapoints, each set of datapoints being located within one of the representation courses; calculate a spline for each set of datapoints; calculate a circumference value of each spline; determine a course pressure to be applied by each material course based on the pressure configuration data; select a material for knitting at least part of the compression garment and determining a number of needles for each representation course based on the course pressure of the associated material course, the material data, the circumference value of the associated spline; and produce a knitting pattern based on the number of needles for each representation course; and a knitting machine for knitting the compression garment based on the or each knitting pattern using said material.

According to a third aspect of the invention there is provided a compression garment made by the method as claimed in any one of the preceding claims. The garment as produced by the method is different to garments not formed by the method. The garment as produced by the method more accurately conforms to the body part as compared to garments not produced by the method.

According to a fourth aspect of the invention there is provided a method of modelling a bespoke knitted compression garment comprising material courses, the method comprising the steps of: a) providing a representation of a body part on which the compression garment is to be worn, the representation comprising a plurality of datapoints; b) defining a plurality of representation courses around the representation, each representation course representing one of the material courses of the compression garment when worn on the body part; c) selecting, for each representation course, a set of datapoints from the plurality of datapoints, each set of datapoints being located within one of the representation courses; d) calculating a spline for each set of datapoints; and e) calculating a circumference value of each spline.

Preferably, the method is computer implemented.

According to a fifth aspect of the invention there is provided a method of providing a matched compression garment to a patient, comprising the steps of: a) providing a representation of a body part of the patient on which the compression garment is to be worn, the representation comprising a plurality of datapoints and including size data corresponding to a size of the body part; b) determining a pressure configuration to be applied by the compression garment on the body part; c) providing a database of pre-existing compression garments having different size data and for applying different pressure configurations; d) selecting a pre-existing compression garment from the database based on matching size data and pressure configuration of the representation to the size data and pressure configuration of the pre-existing compression garment; and e) providing the pre-existing compression garment to the patient.

Preferably, steps a) to d) are computer implemented.

The invention will now be more particularly described, byway of example only, with reference to the accompanying drawings, in which.

Figure 1:
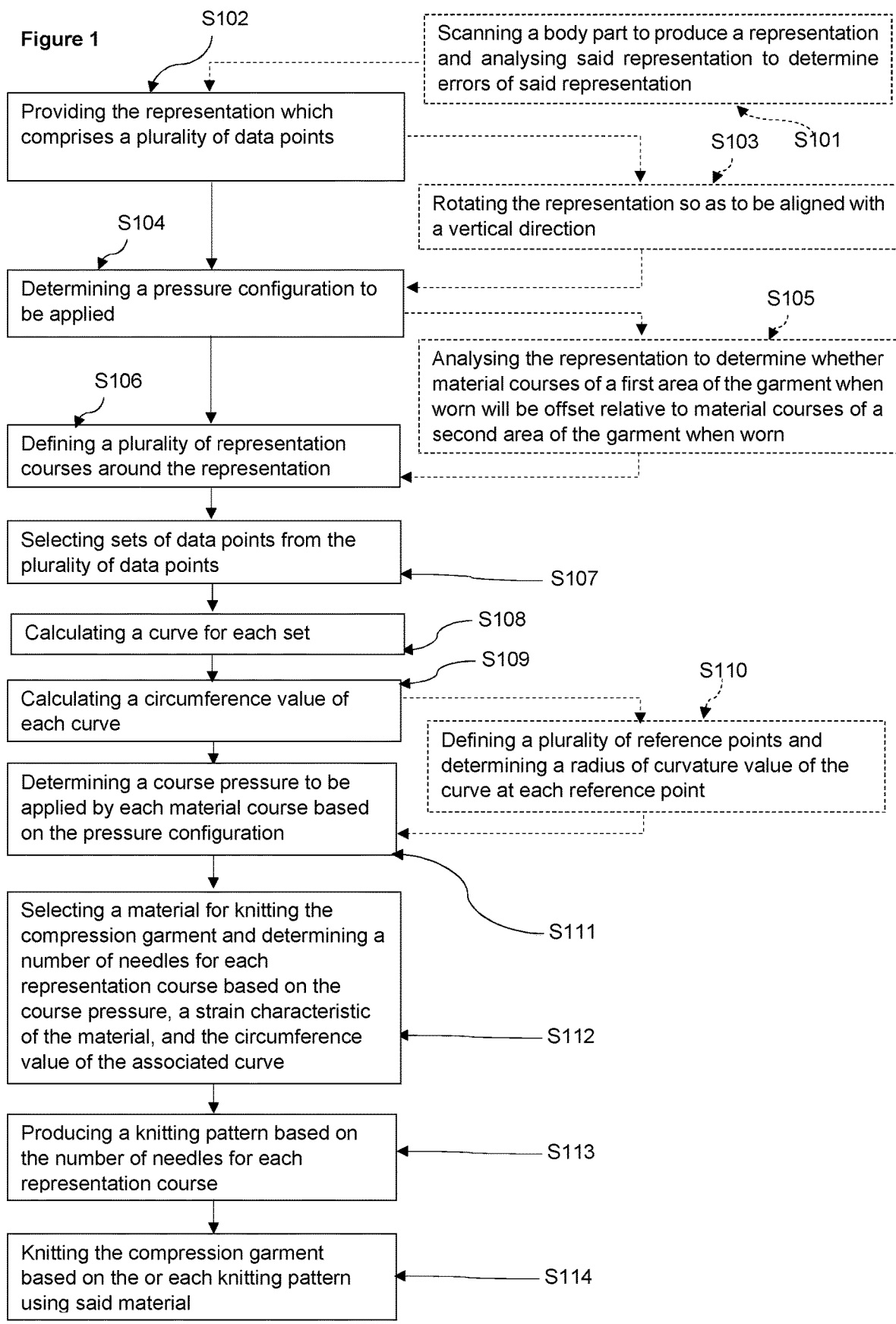
FIG. 1 shows a depiction of an embodiment of a method in accordance with the first and fourth aspects of the invention.

Referring firstly to FIG. 1, there is shown a method of making a bespoke knitted compression garment to be worn on a body part of a patient or user. The method of making a bespoke knitted compression garment includes steps for modelling a bespoke knitted compression garment.

A knitted compression garment may be tubular or substantially tubular in form, particularly if the compression garment is a stocking to be worn on a leg or foot, a sleeve to be worn on an arm, or a binder to be worn around an abdomen. A knitted compression garment comprises a plurality of courses. For flat knitted garments in weft knitting, each course may be considered to be a band, ring or circle of yarn. Adjacent courses or bands of yarn have interconnected or interknitted loops or bights.

The method of making a bespoke knitted compression garment may first comprise a step of scanning S101 a body part to produce a representation of the body part. The scanning S101 may be undertaken by any appropriate scanner, scanning means or scanning setup. For example, the scanning S101 may be carried out by clinician using a camera, such as that on a portable electronic device such as a tablet, to take images or record video of the body part from multiple angles or perspectives. Scanning software may then transform such images or video into a representation, in other words a model or three-dimensional model, of the body part which comprises a plurality of datapoints 10 or vertices. The representation or model is an electronic or computer implemented representation. The representation comprises the plurality of datapoints 10. The representation may also include lines, such as curves, which are fitted to the datapoints to indicate contouring for visualisation purposes.

In the instance that the body part on which the compression garment is to be worn is a leg 12 and foot 14, the representation is preferably such that it includes at least part of both the leg 12 and the foot 14, for example including at least a majority of the foot 14 and at least a majority of the lower leg 12.

For convenience, the scanning S101 may be done with the patient or user having their legs 12 spaced apart and therefore at an angle to a vertical direction. The representation may be provided by the scanning software with respect to a conventional Cartesian coordinate system. As such, the representation, or a longitudinal extent thereof, which is produced via such scanning S101 may be offset relative to an axis which indicates the vertical direction, typically the z-axis Z, compared to an in-use arrangement. The rotation of said representation may therefore be necessary and will be better understood hereinbelow.

Whilst a scanning process S101 is described, it will be appreciated that this may not be necessary to the invention and a representation may instead be provided from an alternative source.

The scan or representation may then be provided to a processor or system by the clinician, along with other information such as a desired pressure configuration to be applied by the garment, the colour of the compression garment, and the number of garments. The information and scan may be provided by the clinician to the processor or system via an order form. The order form may be provided to the system or processor by a human operator, or directly read by the system or processor.

A job queue may be used by the system or processor to appropriately process orders.

If the scanning S101 is incorrectly carried out, then there may be errors in the representation. For example, there may be holes or gaps where insufficient scanning data was recorded to form an accurate representation. The method may therefore comprise the step of assessing S101 or analysing the scan to determine whether there are holes or other errors in the representation. The system uses an appropriate algorithm to achieve this. If there are sufficiently small holes or other errors, then the holes or errors may be automatically filled and therefore the representation completed. The filling of the holes or errors may be accomplished by an appropriate algorithm based on an expected geometry or conforming with a geometry of the representation which surrounds the hole or error. Whilst described as resulting from incorrect scanning, the errors or holes may also arise from the provision of the representation via non-scanning means. For example, in the instance of errors in data transmission.

The size of the hole which may be acceptably or effectively filled may depend on the location of the hole. For example, a hole which is in a leg portion, and in particular a calf portion of the representation, may have a diameter of up to 30 mm. However, a hole which is in an ankle portion may have a diameter of up to 10 mm. This is due to the calf having a greater uniformity and predictability than the ankle.

The representation of datapoints may comprise a plurality of triangles, each side of each triangle having another triangle thereagainst. Holes in the representation exist where triangles are absent, and as such a side of a triangle adjacent to the hole does not have a triangle at said side. The hole may be filled by inserting triangles of best fit into the hole.

The errors may not be able to be corrected automatically, for example if the errors are too large, and therefore re-scanning of the body part may be required, or provision of a new representation may be required. In this instance, the method comprises the step of notifying or alerting the clinician to either re-scan the body part, or obtain a new scan, before subsequent steps are carried out.

The representation or corrected representation may then be provided to the processor or system S102.

Figure 2:
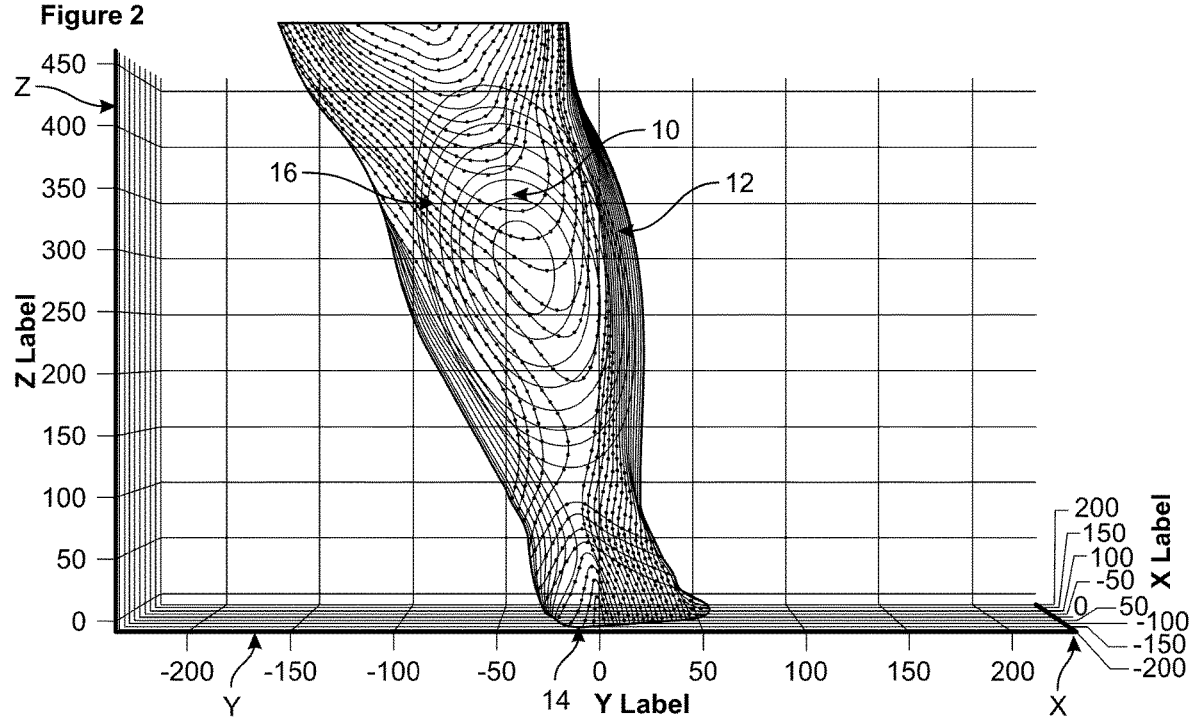
FIG. 2 shows a representation of a leg misaligned from a vertical direction.

As discussed above and shown in FIG. 2, the representation, having been produced by scanning a leg 12 and/or foot 14, may be misoriented and therefore may be a misoriented representation 16. In other words, the representation 16 is in an orientation or at angle relative to the z-axis Z of the coordinate system which is not representative of the body part when the patient or user is in a typical standing condition. As such, said misoriented representation should be transformed or rotated to a correctly oriented condition S103, having an orientation relative to said z-axis Z which is representative of the body part when the patient or user is in a typical standing condition.

This is achieved via rotating said misoriented representation by an angle defined between two markers having different z-axis Z positions, each marker being defined by an average x-axis X or y-axis Y position of respective groups of datapoints 10 of the misoriented representation having the same z-axis Z position.

For example, a first group of datapoints 10 with a z-axis Z position between 101 and 99 are sub-selected. The average y-axis Y position is calculated by averaging the y-axis Y positions of the group to produce a first marker. This is repeated for a second group of datapoints 10 with a z-axis Z position between 201 and 199 to produce a second marker. A linear line is created between the first and second markers. The angle by which the representation needs to be rotated, in other words the angle between the z axis and the line, is calculated using the arctan of the gradient of this linear line, since the representation is being aligned with the z axis.

The datapoints 10 of the representation are then rotated using the following equations:

$$y = y_i \cos \theta - z_i \sin \theta$$

$$z = z_i \cos \theta + y_i \sin \theta$$

Where y is the rotated y coordinate of a datapoint, $y_i$ is the initial or misoriented y coordinate of a data point, $\theta$ is the angle between the linear line and the z axis, $z_i$ is the initial or misoriented z coordinate of a data point, and z is the rotated z coordinate of a datapoint.

Figure 3:
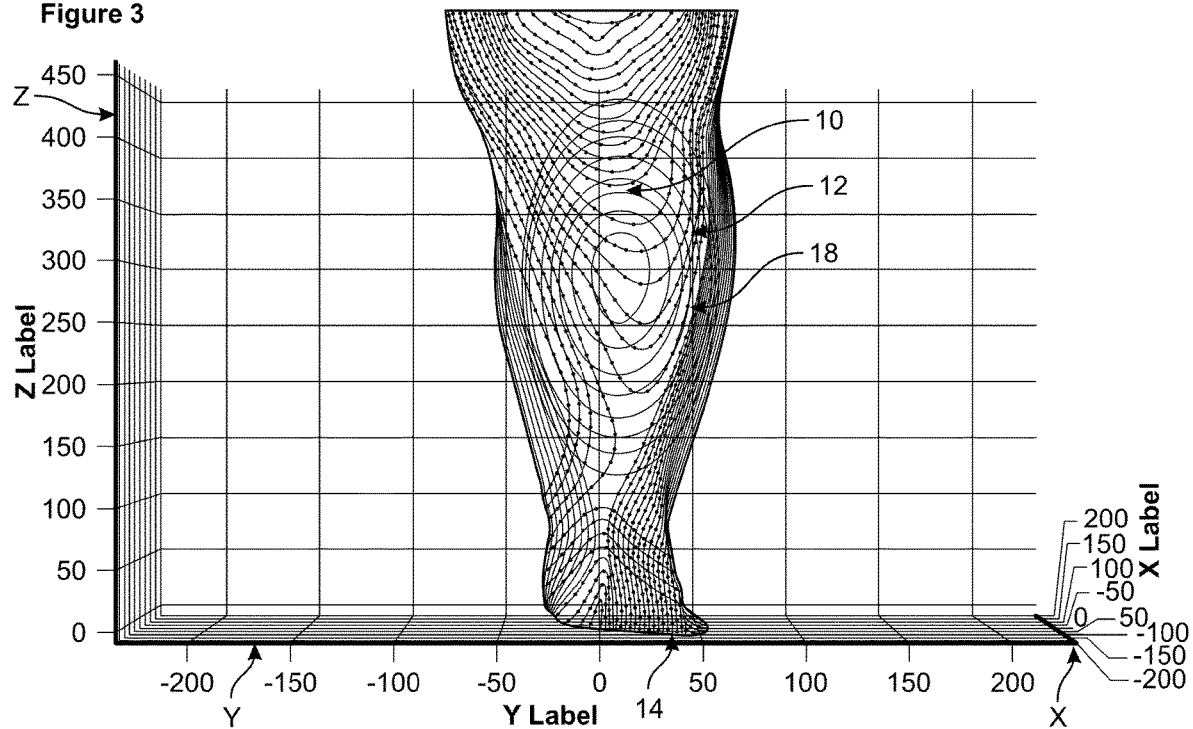
FIG. 3 shows a representation of a leg aligned with a vertical direction.

The misoriented representation is thus correctly oriented, as shown in FIG. 3 to produce a correctly orientated representation 18. The representation 18 is then centred about the x-axis X by calculating the average of the x position value of the datapoints 10 and subtracting it from the x-axis X position of each datapoint. The same process is done relative to the y-axis Y.

A pressure configuration may be defined by the clinician, based on a patient's requirement, and input to the system S104. The pressure configuration may be a uniform pressure arrangement, such that the garment is intended to provide a uniform pressure across the garment, a graduated pressure configuration, such that the garment is intended to apply a higher pressure at one portion of the garment and a decreasing pressure away from this portion, or a different pressure arrangement. The pressure configuration may be input to the processor or system at the same time as the representation is or datapoints 10 are provided to the processor or system. Values of pressure which a garment may apply may be provided in millimetre of mercury mm Hg. Typical clinical values of pressure dinically desirable to apply may be between 14 mm Hg and 50 mm Hg [1333 Pa and 4000 Pa].

Figure 4:
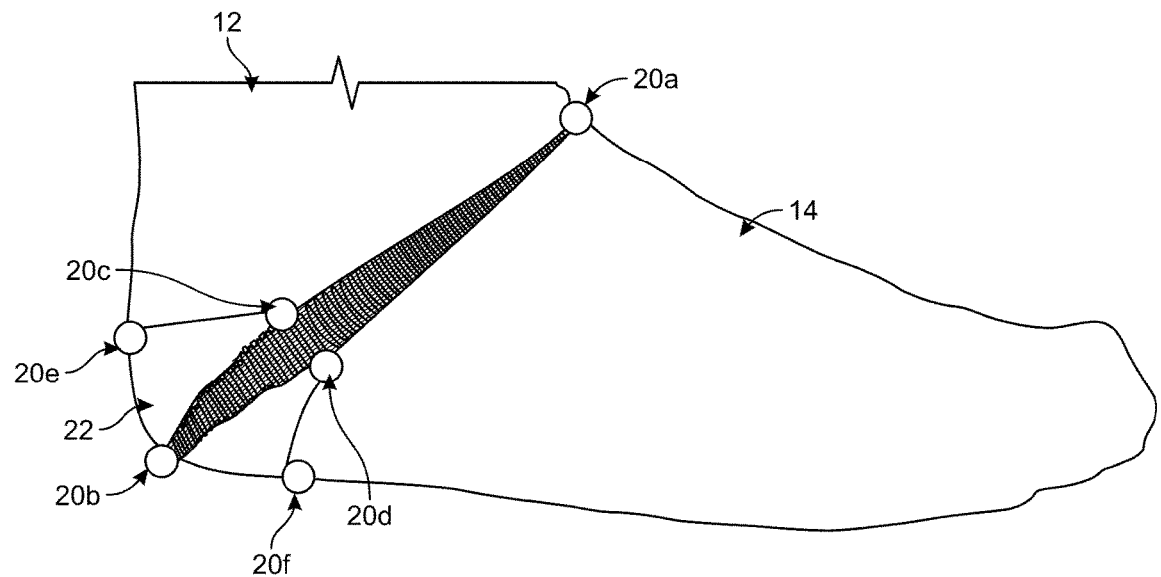
FIG. 4 shows a foot, heel and a portion of a leg, with transition markers which characterise a transition from the leg to the foot.

Referring to FIG. 4, if the body part has areas or portions which are at an angle to each other, the representation 18 should be appropriately, and preferably automatically, analysed to determine the location of these areas S105. This is for the purpose of modelling the likely geometry and orientation of material courses of the garment, when wom on the body part, as representation courses on the representation 18. This will be understood with reference to the leg 12 and the foot 14, where it will be appreciated that an axial direction of the material courses of the foot area 14 of the tubular compression stocking will be parallel or substantially parallel or aligned or substantially aligned with a horizontal axis when wom on the body. Contrastingly, an axial direction of the material courses of the leg area 12 of the tubular compression stocking will be parallel or substantially parallel or aligned or substantially aligned with a vertical axis when wom on the body. Therefore, the foot and leg areas 14, 12 of the body should be identified so that representation courses can be appropriately modelled around the relevant body part area.

This may be achieved by determining at least one transition point 20a, 20b, 20c, 20d, 20e, 20f which characterises a transition between leg 12 and foot 14. Relevant transition points 20a, 20b, 20c, 20d, 20e, 20f are shown in FIG. 4. These demarcate the leg area 12 from a heel area 22 and the foot area 14 from the heel area 22.

A first transition point 20a at a forward most surface of the representation 18 may firstly be automatically identified. The first transition point 20a is identified by firstly identifying the forward most datapoints 10 which would define the forward most surface 24 of the leg 12 and foot 14. In other words, the datapoint with the maximum x-value for each group of datapoints 10 which have the same or similar z-value.

Said datapoints 10 may be sub-selected based on typical transition point characteristics to improve accuracy of identification by reducing the number of datapoints 10.

Figure 5:
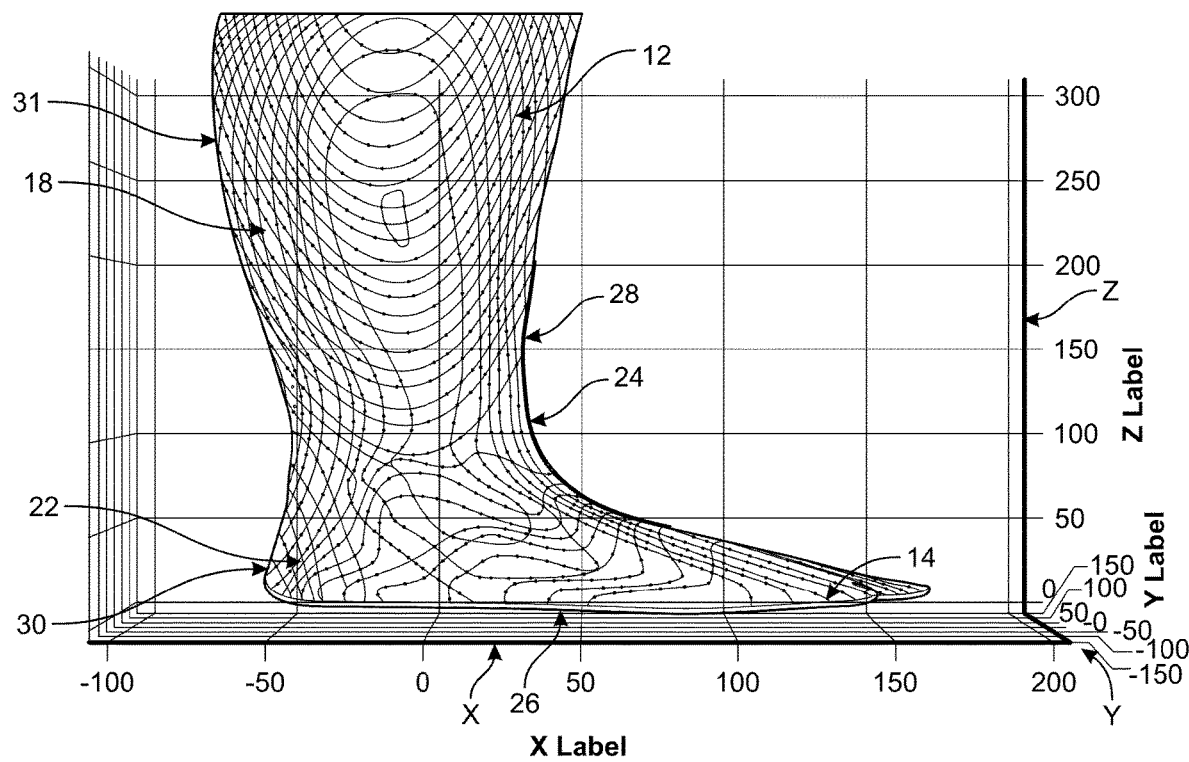
FIG. 5 shows a representation of a foot, heel and a portion of a leg with a selected portion of forwardmost datapoints of the representation highlighted.

For example, the forward most datapoints 10 may be sub-selected by selecting those which are 40 mm and 200 mm above a lowest point 26 of the representation 18, or having a z-axis Z value or position therebetween, and more particularly between 45 mm and 200 mm. The datapoints 10, and a spline function or best fit curve 28 calculated therefor, according to this sub-selection is indicated in FIG. 5.

The sub-selection of datapoints 10 may then be further sub-selected by selecting those datapoints 10 of the sub-selection which are within 50 mm, in a forward direction, of the rearwardmost datapoint of the sub-selection. In other words, sub-selecting those datapoints 10 which have an x-axis X position within 50 mm in an x-axis X direction of the datapoint of the sub-selection which has the minimum x-axis X position. This produces a further sub-selection.

The further sub-selection may be further sub-selected by selecting those datapoints 10 of the further sub-selection which are less than 50 mm above the lowest datapoint of the sub-selection. In other words, selecting those datapoints 10 of the further sub-selection which are less than 50 mm away from the datapoint with the minimum z-axis Z position in the z-axis Z direction of the further sub-selection. This produces a further refined sub-selection of datapoints 10.

A first curve may then be calculated for the further refined sub-selection. For example, a spline may be calculated based on the sub-selected datapoints 10. The first transition point 20a is found by determining a point of maximum change in gradient of the first curve.

A second transition point 20b at a rearmost surface 30 of the representation 18 may additionally or alternatively be calculated. The second transition point 20b is identified by firstly identifying the rearmost datapoints 10 which would define the rearmost surface 30 of the leg 12 and foot 14. In other words, the datapoint with the minimum x-value for each group of datapoints 10 which have the same or similar z-value.

Said datapoints 10 may be sub-selected based on typical transition point characteristics to improve accuracy of identification by reducing the number of datapoints 10. However, it will be appreciated that such a sub-selection may not be necessary.

The sub-selection may be based on those datapoints 10 which are within 10 mm of a rearmost datapoint 31, in other words those datapoints 10 which have an x-axis X position within 10 mm in an x-axis X direction of the datapoint of the selection which has the minimum x-axis X position. A further or alternative sub-selection may be based on those datapoints 10 which are within 10 mm of the lowest datapoint 26 of the representation 18 or sub-selection, in other words those datapoints 10 which have an z-axis Z position within 10 mm in an z-axis Z direction of the datapoint of the selection or representation 18 which has the minimum z-axis Z position.

A second curve may then be calculated for the sub-selection. For example, a spline may be calculated based on the sub-selected datapoints 10. The second transition point 20b is found by determining a point of maximum change in gradient of the second curve.

Figure 6:
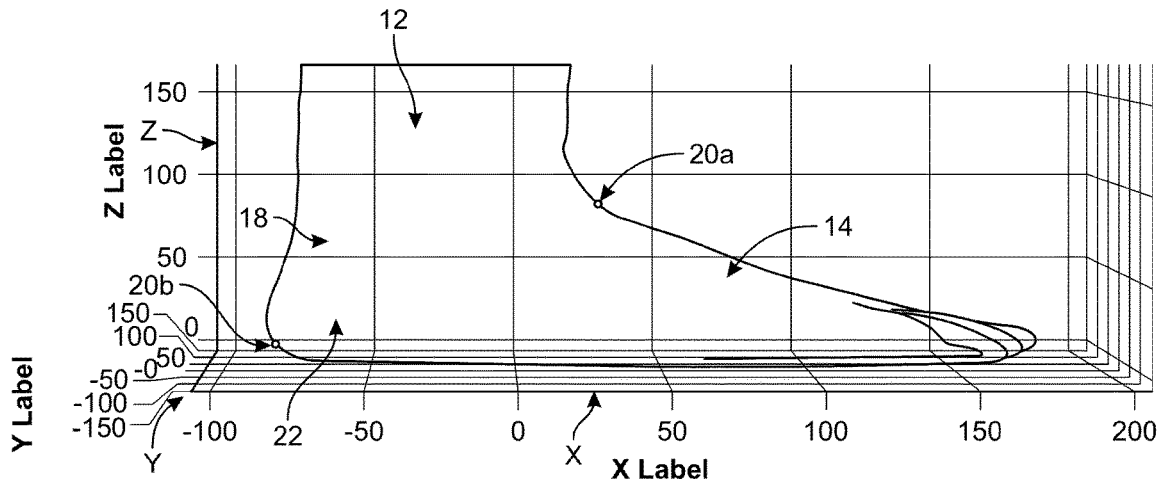
FIG. 6 shows the representation of FIG. 5 with transition markers indicated.

The identified first and second transition points 20a, 20b are indicated in FIG. 6.

Further transition points 20c, 20d, 20e, 20f may be identified in a similar or identical way. The transition points here define the shape of the heel portion 22 of the representation 18. However, it will be appreciated that further transition points may not be necessary.

Furthermore, it may be that only the first or second transition point 20a, 20b may be calculated, and the remaining transition points approximated. For example, only the first transition point 20a may be calculated as above. An intermediate reference point or line may be defined 50 mm or substantially 50 mm from a lowest point of the representation 18 and 50 mm or substantially 50 mm from a most backward point of the representation 18. For example, 55 mm from a lowest point of the representation 18 and 55 mm from a rearmost point of the representation 18. Although 50 mm or substantially 50 mm is described, it will be appreciated that depending on the size of the body part, this value may be within the range of 40 mm to 60 mm. A third reference point 20c or line is 6 mm backward of this intermediate reference point and a fourth reference point 20d is 6 mm below this intermediate reference point. Although the third and fourth reference points 20c, 20d are described as 6 mm away from the intermediate reference point, it will be appreciated that depending on the size of the body part, this value may be within the range of 4 mm to 8 mm. The second transition point 20*a* may be defined at an intersection between the rearmost surface 30 and a line which extends from the first transition point 20*a* and along a direction between the first transition point 20*a* and the intermediate reference point.

Alternatively, the second transition point 20*b* may be calculated first. This may be done via the previously described method relating to the maximum change in gradient of the second curve. However, it will be appreciated that the second transition point may be determined via other means, such as being manually selected. The second transition point 20*b* may otherwise be referred to as a point which defines a back of a heel. The first transition point 20*a* may then be determined by selecting the datapoint of the forwardmost datapoints, or a sub-selection thereof, which is closest to the second transition point 20*b*. In other words, a hypotenuse between the second transition point 20*b* and each datapoint of the forwardmost datapoints may be calculated, and the smallest hypotenuse value determines the closest datapoint. Whilst it is preferred that an actual forwardmost datapoint defines the first transition point 20*a*, it will be appreciated that a curve, spline, or convex hull based on the forwardmost datapoints may be calculated, and a point on the curve which is closest to the second transition point 20*b* may define the first transition point 20*a*. However, it will be appreciated that not all transition points may be required to be calculated, and the heel area 22 may be disregarded, with only the transition between leg 12 and foot 14 being calculated.

The fifth and sixth transition points 20*e*, 20*f* may not be transition points as such, and may simply indicate the rearwardmost point of the leg 12 and lowest most point of the foot 14 respectively. Alternatively or additionally, the location of the fifth transition point 20*e* may be determined by the intersection of the rear surface of the leg 12 with a line which extends from the third transition point 20*c* and is parallel with the x-axis X. Similarly, the location of the sixth transition point 20*f* may be determined by the intersection of the lower surface of the foot 14 with a line which extends from the fourth transition point 20*d* and is parallel with the z-axis Z.

Figure 7:
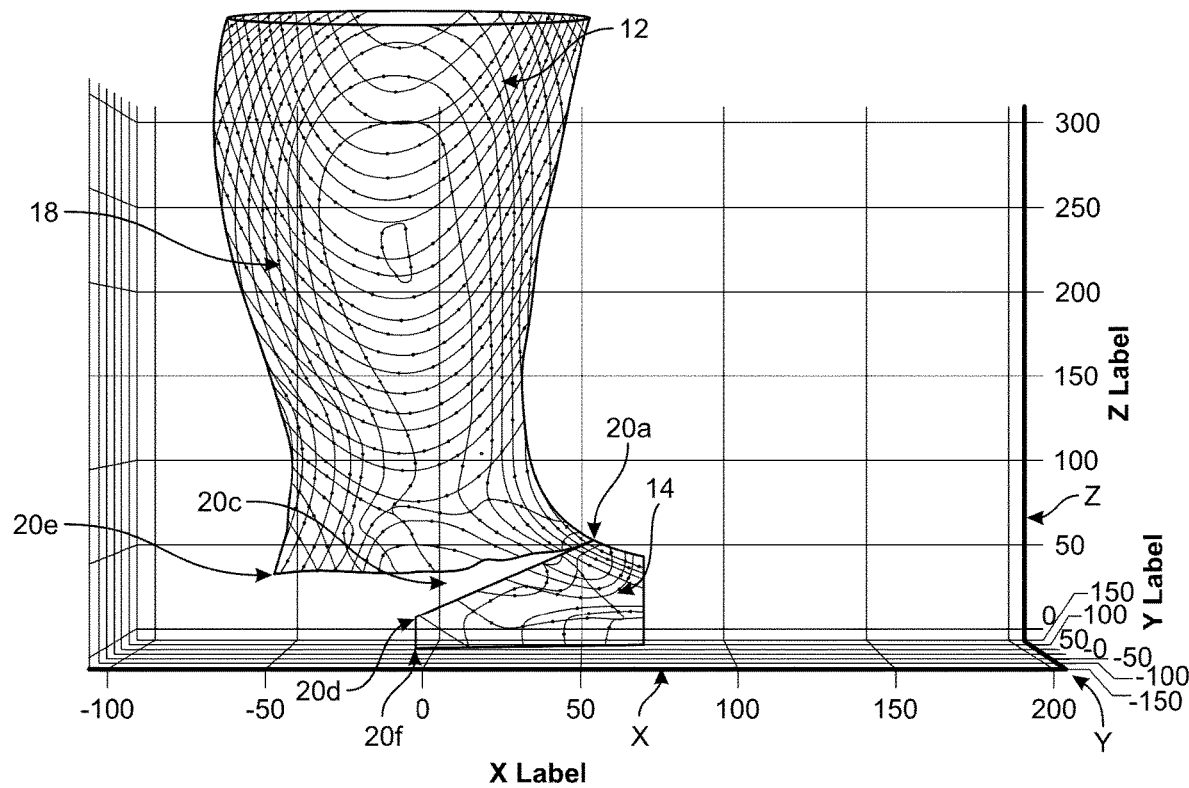
FIG. 7 shows the representation with determined foot and leg areas highlighted.

The selection of the datapoints 10 of the leg 12 and the foot 14 are shown in FIG. 7. A forwardmost portion of the foot is here omitted from selection, as is a heel portion 22. The design and manufacture of the heel portion 22 and forwardmost portion of the foot, or in other words a toe portion, will be better understood hereinbelow.

The orientation and geometry of the representation courses are preferably set to accurately reflect the material courses of the garment. For example, the axial direction of each of the representation courses of the foot 14 potion should be oriented so as to be horizontal or substantially horizontal. Similarly, the axial direction of each of the representation courses of the leg 12 portion is orientated so as to be vertical or substantially vertical.

Figure 8:
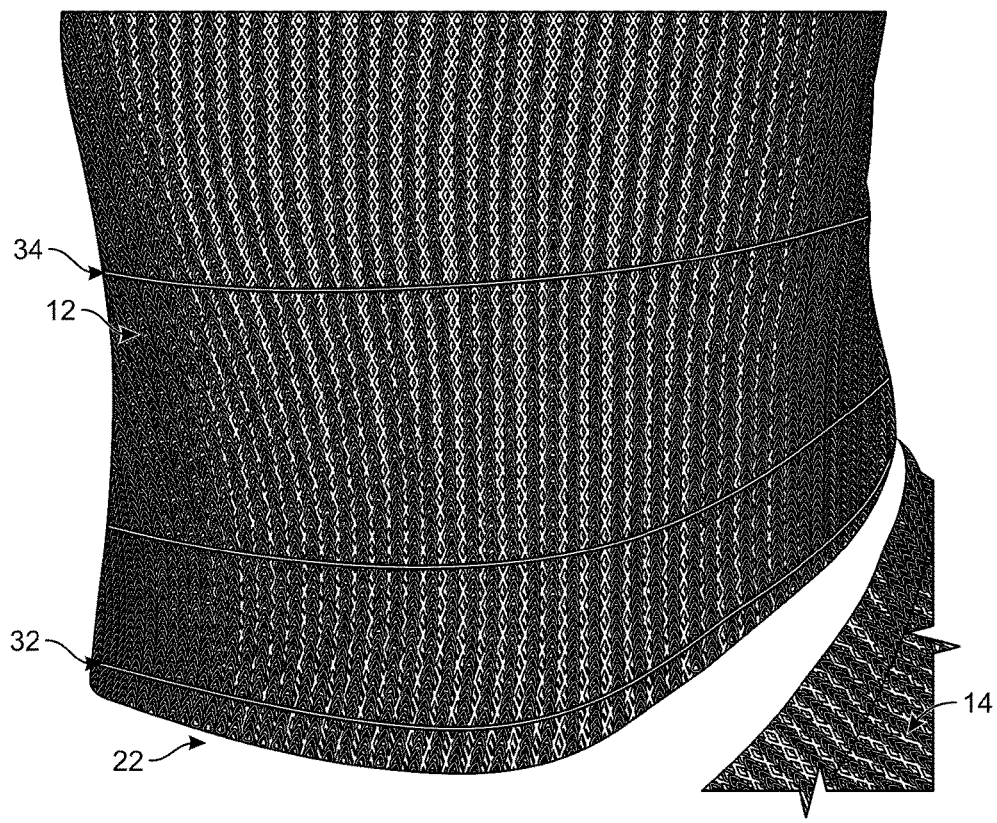
FIG. 8 shows a lower portion of a leg area of a compression garment worn by a user, indicating a path of three material courses.

Those representation courses of the leg 12 and foot 14 which are proximate to the heel 22 may be modelled to be non-planar, for example being curved. The benefit of this is can be identified with reference to FIG. 8 which indicates that a first material course 32 proximate to the heel 22 is more curved or non-planar than a second material course 34 distal to the heel 22. Thus, the geometry of the representation courses should reflect this to accurately model the material courses. Thus is since, if the non-planar or curvate character of the courses is not modelled, an accurate value of circumference of the non-planar or curvate course cannot be calculated given that a non-planar course typically has a greater circumference than a planar course.

As such, those representation courses proximate to the heel 22 may be modelled as non-planar or curved.

In particular, those representation courses which are within 50 mm of the first transition point 20*a* in a direction parallel with the z-axis Z may be required to be modelled as non-planar. However, it will be appreciated that this may vary depending on the geometry of the body part, for example being between 25 mm and 100 mm of the first transition point 20*a* in a direction parallel with the z-axis Z.

Figure 9:
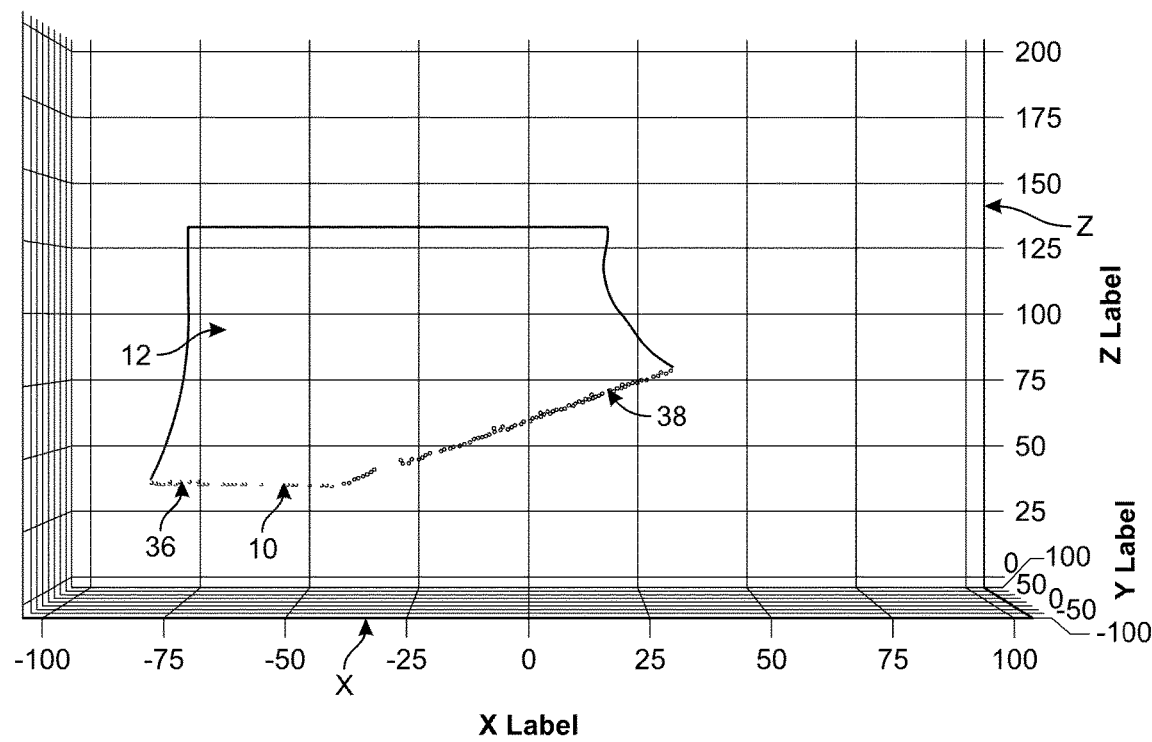
FIG. 9 shows a non-planar representation course being modelled as two planar portions.

To simplify calculations, the non-planar representation courses are preferably modelled as two planar portions at an angle to each other. This is indicated in FIG. 9. This may be achieved with an algorithm to best fit two planar portions to the curved course. Preferably, a first 36 of the planar portions is horizontal, in other words parallel to the x-y plane, and a second 38 of the planar portions is at an angle to the horizontal or x-y plane, and preferably at a non-perpendicular angle to the horizontal or x-y plane. As shown in FIG. 9, the representation courses would comprise a plurality of datapoints 10.

The shape of the non-planar courses may be dependent on the location of the first, third and fifth transition points 20*a*, 20*c*, 20*e*. For example, a representation course proximalmost to the heel portion 22 may be defined directly using these points. The first planar portion 36 may be defined as being between the fifth and third transition points 20*e*, 20*c*. The second planar potion 38 may be defined as being between the third and first transition points 20*c*, 20*a*. A representation course which is proximalmost to the heel 22 and which is planar, for example a representation course 50 mm away from the first transition point 20*a* may be aligned with the x and/or y axis X, Y. Intervening non-planar representation courses may have a decreasing non-planarity between the non-planar representation course proximalmost to the heel portion 22, and the planar representation course which is proximalmost to the heel 22. In other words, an angle between the first and second planar portions 36, 38 may increase for representations between the non-planar representation course proximalmost to the heel portion 22, and the planar representation course which is proximalmost to the heel 22. The angle may linearly increase, or may non-linearly increase.

The method comprises the step S106 of the system dividing the representation 18 into the plurality of representation courses, based on a length of the desired garment and the height or spacing of each course. In other words, bands are defined around the representation 18, the bands having a given height. For example, the garment or representation 18 may be 300 mm in length, and an average or typical course height may be 0.75 mm, resulting in 400 representation courses defined around the representation 18. The course height may be selected based on the type of material for the yarn, and/or the desired properties of the garment. Other garment lengths and course heights may be considered.

Non-planar material courses of a garment when worn on a body part are typically more stretched at the back and less stretched or looser at the front. As such the system or processor preferably adjusts the curved or non-planar representation courses to have a greater course height at or adjacent to the front and a lesser course height at or adjacent to the rear. As such, the course height of the non-planar representation courses may not be uniform.

In a similar way, material courses having a greater circumference value may have a lower course height due to manufacturing techniques. So different representation courses may have different course heights depending on the circumference.

Although it is preferable that material courses having a greater circumference value may have a lower course height, it will be appreciated that this may not be the case. For example, a uniform course height may be used providing a given number of courses for a given height of garment. The value of the course height may then be refined and adjusted using an algorithm which predicts the variance of course height due to the manufacturing technique.

A set of datapoints 10 for each representation course is selected S107 by the processor, each set of datapoints 10 being located within the corresponding representation course. In other words, the datapoints 10 which have coordinates within the boundaries defined the representation courses are grouped into sets associated with the relevant representation courses.

Those sets which are associated with representation courses which are planar or substantially planar may be modelled as flat. The difference in height or z-axis Z position between datapoints 10 of such a set which may arise due to the non-zero value of the course height may be disregarded.

Figure 10:
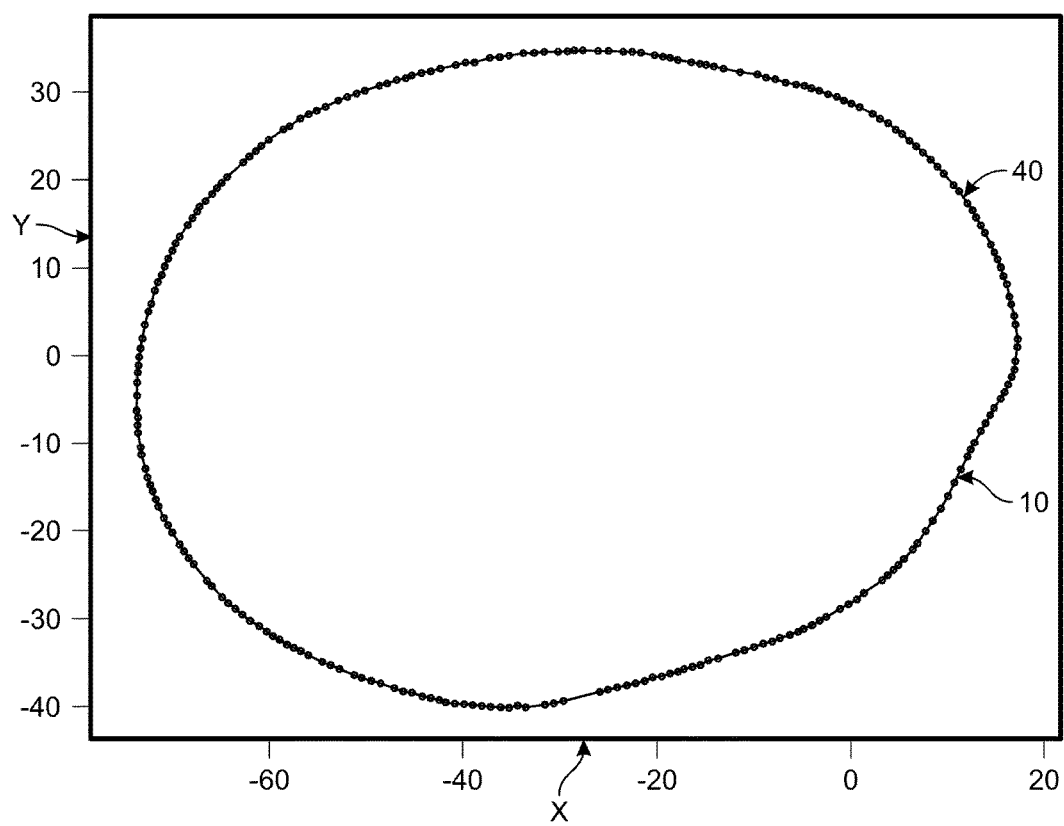
FIG. 10 shows a set of datapoints of a representation course and a corresponding spline calculated for said set.

A spline 40, and in particular a basis spline or B-spline, function of best fit may be calculated S108 by the system based on the datapoints 10 of each planar set. Such a B-spline 40, with associated datapoints 10, is shown in FIG. 10. Here the spline function 40 can be seen to extend through each datapoint, although it will be appreciated that this may not be the case. Although a spline 40 is described, it will be appreciated that other curve fitting or curve approximation techniques or functions may be considered. Since the spline 40 is calculated based on the raw datapoints 10, rather than based on an approximation of the datapoints 10 or based on boundary curves, contours or surfaces which are in turn based on the datapoints 10, the spline 40 is more representative of the body part.

Although this may not be shown in FIG. 10, it is preferable that the spline or other curve is a convex hull, such that it is the smallest convex set or convex shape which contains all the datapoints of each set. In such a case, it will be appreciated that a spline or B-spline may not be used, or if it is used, the datapoints which would fall inside the convex set may be ignored for generating the spline. Although a convex hull is preferred, it will be appreciated that the smallest convex set may not actually be required, and that a larger convex set may be used.

Before calculating the spline 40, the datapoints 10 may be required to be centred around x and y axes. This can be done via calculating the average of the x-axis X position value of the datapoints 10 and subtracting it from the x-axis X position of each datapoint. The same process is done relative to the y-axis Y. The datapoints 10 can then be converted to polar coordinates to obtain an angular, or azimuth, value of each datapoint around a centre or origin of the datapoints. The datapoints 10 are then sorted by the angular, or azimuth, value. This is to prevent or limit the datapoints 10 being assigned an incorrect order around the origin when calculating the spline. The B-spline 40 can then be calculated.

For sets of datapoints 10 associated with non-planar courses, at least some of the datapoints 10 may have differences in height or z-axis Z position which require consideration to provide a spline which is representative of the associated material course. As such, if the non-planar representation is modelled as two planar portions at an angle to each other, one planar portion may be rotated relative to the other planar portion so as to be coplanar. For example, the portion 38 which is at an angle to the x-y plane is rotated so as to be parallel with the x-y plane. This rotation may be done in a similar or identical way as the rotation of the representation 18 relative to the z-axis Z as previously described.

Having rotated or transformed the datapoint set of the or each non-planar representation course, a B-spline may be calculated as previously described.

The method further comprises a step S109 of a circumference or perimeter value for each spline 40 circumference being calculated by the system. This may be done via the formula:

$$C = (x'^2 + y'^2)^{0.5}$$

Where C is the circumference of the spline, x' is a first derivative of x for example the first derivative of x with respect to y, and y' is a first derivative of y for example the first derivative of y with respect to x.

The method may further comprise the step S110 of the system defining a plurality of reference points on or around the circumference of the spline 40. For example, each spline 40 may have 500 reference points defined thereon. Alternatively, or additionally, the circumference value of the spline 40 may be used to determine the number of reference points, for example if the circumference value was 100 mm, 100 reference points could be used per 1 mm, or 200 reference points per 0.5 mm.

A radius of curvature may be defined at each reference point using the formula:

$$r_r = \frac{|(x'y'') - (y'x'')|}{(x'^2 + y'^2)^{3/2}}$$

Where $r_r$ is the radius of curvature at a reference point, x" is a second derivative of x for example the second derivative of x with respect to y, and y' is a second derivative of y with respect to x.

Additionally, the splines 40 may be analysed to identify concave and convex areas.

The method further comprises a step S111 of determining a pressure value of pressure to be applied by each material course based on the pressure configuration. The representation course associated with the material course is associated with this pressure value.

The method further comprises a step of selecting a material for knitting at least part of the compression garment and determining a number of needles for each representation course based on the course pressure of the associated material course, a strain characteristic of the material, and the circumference value of the associated spline S112. This involves the system selecting a material to knit the courses. This may be from a selection of suitable materials known to the skilled person. Alternatively, there may only be one possible material for use with the system.

The material may be selected based on values or characteristics of a stress-strain curve, or a curve similar to a stress-strain curve, of a material. Whilst described as a stress-strain curve, it will be appreciated that this may in fact be a force-extension curve, or a force-strain curve One characteristic is the y-intercept of material coefficient, which may be the y-intercept of a tangent to the curve divided by the thickness or cross sectional area of the material being tested, or twice the thickness of the material being tested if two thicknesses of material are being tested. This may be an equipment normalisation stress. The tangent to the curve may be drawn at a linear portion of the curve. An initial portion of the curve is non-linear, after which there is the linear portion to which a tangent is to be drawn. Although described as a linear portion, the portion may be non-linear, and therefore the tangent or tangent equivalent may be a polynomial function. Another characteristic is the gradient material coefficient, which may be equivalent to, similar to or dependent upon the Young's modulus. The gradient material coefficient may be the gradient of the aforementioned tangent divided by the thickness or cross-sectional area of the material, or twice the thickness of the material being tested if required.

A number of needles or wales for each representation course which would achieve the desired course pressure is then calculated as part of the step S112 based on the material characteristics, the circumference of the associated spline 40 and the radius of curvature values at the reference points of the associated spline 40.

The pressure applied by a course can generally be calculated according to the following first pressure equation:

$$p = \frac{y_{mc} + \nabla_{mc}\varepsilon}{r}$$

Where p is the pressure applied by the course, $y_{mc}$ is the y-intercept of material coefficient, $\nabla_{mc}$ is the gradient material coefficient, $\varepsilon$ is strain of the course, and r is the radius of curvature of the course.

To use the individual radius of curvature values at the reference points in this calculation, the y-intercept of material coefficient is divided by a first individual radius of curvature value. This is added to the y-intercept of material coefficient divided by a second individual radius of curvature value, and so on until a sum of all of the y-intercept of material coefficient divided by the radius of curvature values of the reference points of a spline 40 is calculated. This sum may be represented by $y_r$.

Similarly, the gradient material coefficient is divided by a first individual radius of curvature value. This is added to the gradient material coefficient divided by a second individual radius of curvature value, and so on until a sum of all of the gradient material coefficient divided individually by the radius of curvature values of the reference points of a spline 40 is calculated. This sum may be represented by $\nabla_r$.

The initial equation may then be rearranged to calculate the required strain to achieve the desired pressure of the course.

$$\varepsilon = \frac{pn_r - y_r}{\nabla_r}$$

Where $n_r$ is the number of reference points.

The number of needles is then calculated based on the required strain of the course, according to the following equation:

$$n_n = \frac{C}{1 + \varepsilon w_n}$$

Where $n_n$ is the number of needles used to knit a material or knitted course based on the corresponding representation course, C is the circumference value of the spline 40, and $w_n$ is the width of the needle.

The number of needles for each course can alternatively be calculated via rearranging of the following second pressure equation:

$$p = \frac{1}{a}\left(\frac{1}{N} - \frac{b}{r}\right)$$

where p is desired pressure to be applied, a is a first fabric coefficient and is analogous to $\nabla$mc, b is a second fabric coefficient and is analogous to ymc, r is the local radius of curvature, and N is the number of needles used in knitting the course.

This characteristic equation is a refactoring of the following equation:

$$\frac{r}{N} = aPr + b$$

Based on the Laplace equation above, Pr is proportional to tension T in the fabric when a loop of material knitted using N knitting needles is extended by the machine.

It has been determined that, since the garment to be knitted must be physically manufactured, the interface pressure can be categorised in terms of the physical manufacturing parameters. It is only possible to manufacture garments with an integer number of needles at each course, that is, the horizontal yam of the knit. Given that the pressure exerted on a known radius of curvature is being investigated, the ratio r/N can be used as a surrogate for strain. A plot of r/N against tension thus yields the pair of characteristic coefficients a and b, where a is the gradient and b is the intercept of the plot. b can thus be envisioned as the zero-tension radius of curvature fora garment material for a given needle number construction, whilst a is the corollary of the Young's modulus of the fabric, and will be related to the Young's modulus by a scalar multiplier.

Although the radius of curvature at the reference points of the associated spline 40 are used to improve an accuracy of the pressure applied by the compression garment, it will be appreciated that the spline 40 could be approximated to be a circle and a single radius of curvature for said circle be used to calculate the pressure.

It will be appreciated that different materials may be used for different courses, and that materials may be selected on other criteria, such as colour.

If utilising the first pressure equation, the pressure applied at individual reference points using the material characteristics and the strain value of the course with the following equation:

$$p = \frac{y_{mc} + \nabla_{mc}\varepsilon}{r_r}$$

If utilising the second pressure equation, $\nabla$mc and ymc may be replaced with a and b respectively, and $\varepsilon$ may be replaced with r/N.

Figure 11:
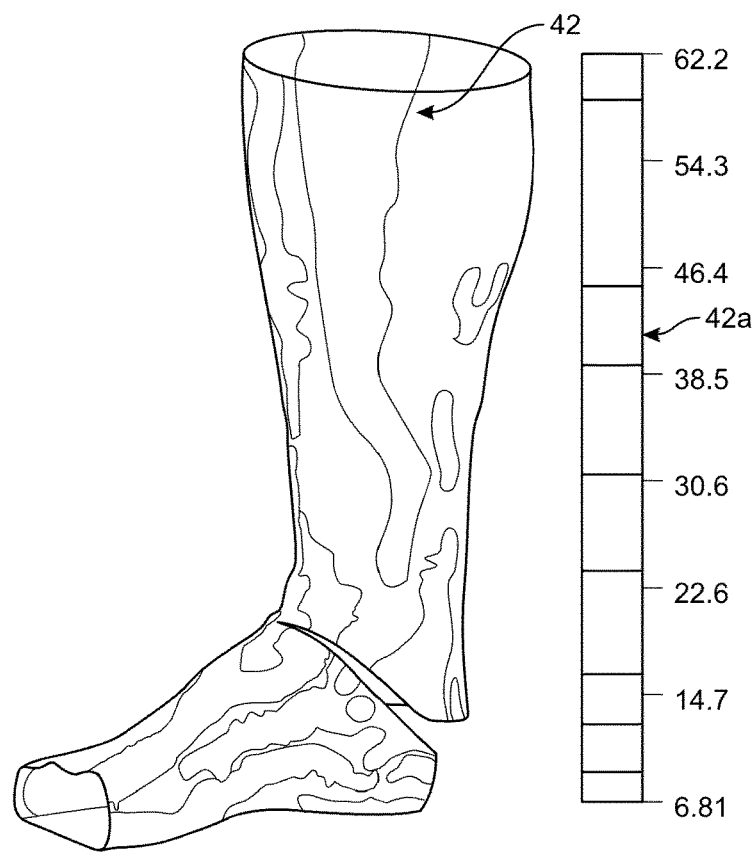
FIG. 11 shows a pressure map which indicates a location and magnitude of pressure applied by a modelled compression garment when worn by a user.

The method may therefore further comprise the step of plotting the pressure values at the reference points to produce a pressure map 42 as shown in FIG. 11. FIG. 11 includes a scale 42*a* for pressure in units of millimetre of mercury, which is the preferred industry unit of pressure. The values provided on the scale may be equivalent to 908 Pa, 1960 Pa, 3013 Pa, 4080 Pa, 5133 Pa, 6186 Pa, 7239 Pa and 8293 Pa.

Figure 12:
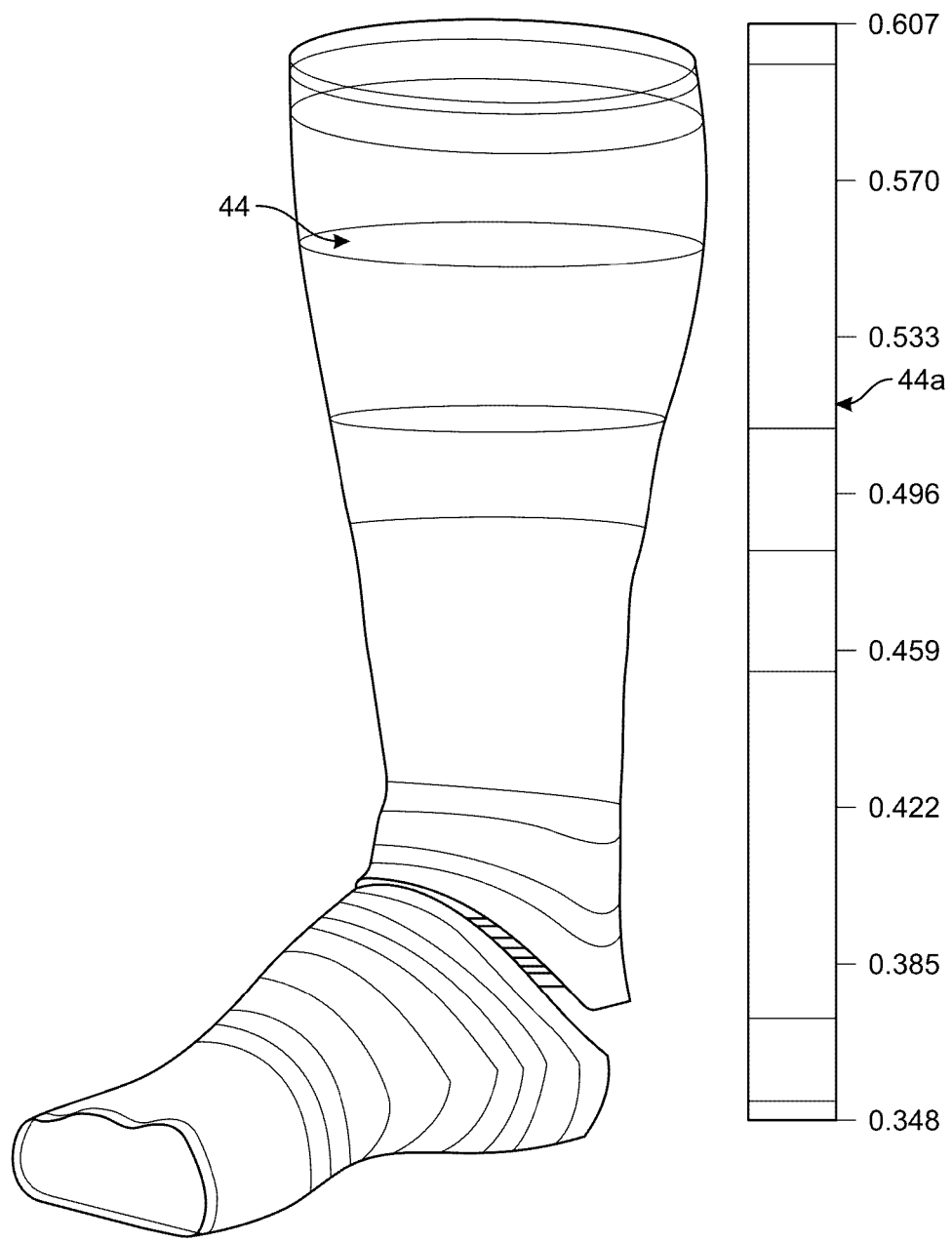
FIG. 12 shows a strain map which indicates a location and magnitude of the strain applied by the modelled compression garment of FIG. 10 when worn by a user.

The method may similarly comprise the step of plotting the strain values of the courses to produce a strain map 44, as shown in FIG. 12. FIG. 12 includes a scale 44*a* for strain.

Such maps 42, 44 may be provided to the clinician for review before knitting of the garment to confirm that the garment would provide a suitable pressure and strain configuration. For example, the clinician may review whether the garment would apply unacceptably high local pressure values. Alternatively, this may be automatically reviewed, with parameters for maximum local pressure, or strain values, being set. Alternative materials may be selected or adjustment of the shape of the course, if local pressure values, or strain values, exceed such parameters.

The above steps preferably apply for leg 12 and foot 14 portions of the representation 18. The heel portion 22 of the garment may be designed as follows. Heel representation courses may be defined for the heel 22. A heel representation course which is proximalmost to the leg 12 may be accorded a similar or identical number of needles as the proximalmost representation course of the leg 12. Similarly, a heel representation course which is proximalmost to the foot 14 may be accorded a similar or identical number of needles as the proximalmost representation course of the foot 14. In this way, the heel portion 22 is partly bespoke to the patient.

Between these two courses, intervening heel representation courses may be defined which form a pocket. This may be termed a reciprocal heel. The intervening heel representation course proximalmost to the leg may be a half course. In other words, it may have half of the course width of the heel representation course which is proximalmost to the leg. The next most proximalmost intervening heel representation course may be a half course with at least one fewer needle. This may continue so that a central intervening heel representation course is a quarter course. In other words, it may have a quarter of the course width of the heel representation course which is proximalmost to the leg and/or foot 12, 14. The next intervening heel representation course may be a quarter course with at least one additional needle. This may continue until the intervening heel representation course proximalmost to the foot 14 is a half course. The portion of the heel representation course which is proximalmost to the leg 12 and not adjacent to the half intervening heel representation course may be knitted to the portion of the heel representation course which is proximalmost to the foot 12 and not adjacent to the half intervening heel representation course. In this way, the heel is formed.

Although half and quarter courses are suggested, it will be appreciated that the heel may have other proportions of the proximalmost representation course of the leg or foot. Additionally, although the heel is described as being symmetric, with the central intervening heel representation course being the smallest, it will be appreciated that this may not be the case.

A toe portion of the garment may be designed and knitted in a conventional manner. Additionally or alternatively, representation courses for the toe portion may be defined according to data points of the representation.

Figure 13:
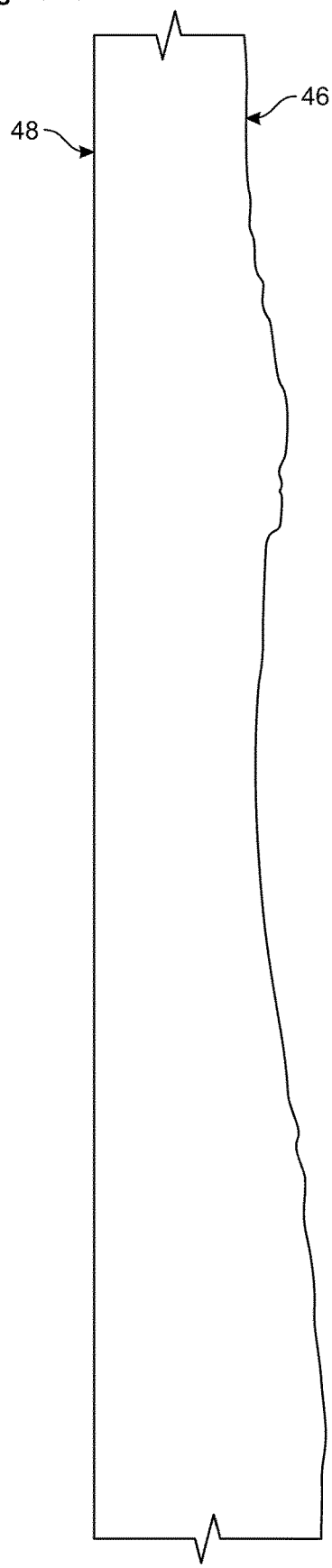
FIG. 13 shows a first embodiment of a knitting pattern with the knitting pattern courses aligned at a front edge and the knitting pattern having not been smoothed.

The method may further comprise the step S113 of producing a knitting pattern based on the number of needles for each representation course. The knitting pattern, or raw knitting pattern, is represented in FIG. 13. The knitting pattern comprises a series of lines 46 adjacent to each other arranged in a top-to-bottom direction. Each line represents a material course which will be knitted, and may be described as a knitting course. A length of the line indicates the number of needles of the course. A left-to-right position of each line relative to adjacent lines indicates an offset of the courses. For example, as shown in FIG. 13, all of the lines of the knitting are aligned along one side 48, to the left, and as such a garment knitted to according to the knitting pattern would have all courses aligned along one side. It will be appreciated that such a garment would not have shaping along this side. This may be advantageous for typical patients who have a flat portion on a lower leg 12, formed by the shin bone.

Figure 14:
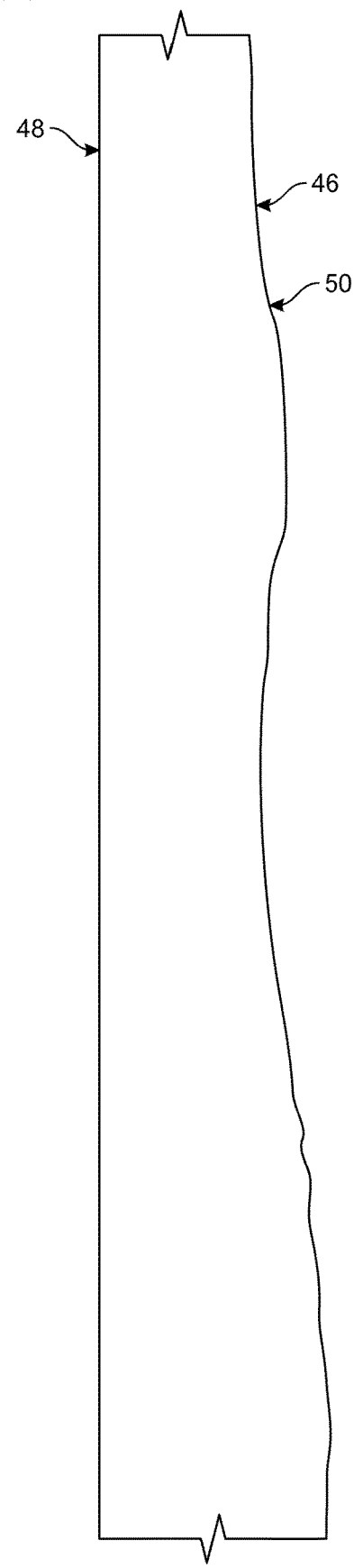
FIG. 14 shows the knitting pattern of FIG. 13 having been smoothed.

The raw knitting pattern may have too much variability in the number of needles, which may increase a risk of dropping stiches. In other words, the knitting pattern may be too rough. The knitting pattern may be smoothed to reduce or prevent the dropping of stiches. The knitting pattern may be smoothed via the use of an algorithm, which may, for example, adjust the number of needles of the lines so that each line of the smoothed knitting pattern has at least four adjacent lines having an equal or substantially equal value of needles. At least a portion of the knitting pattern consists of groups 50 of lines of equal or substantially equal value of needles, each group having at least five lines or knitting courses. However, other group numbers may be considered, for example at least two. The knitting pattern of FIG. 14 has been smoothed accordingly.

Figure 15:
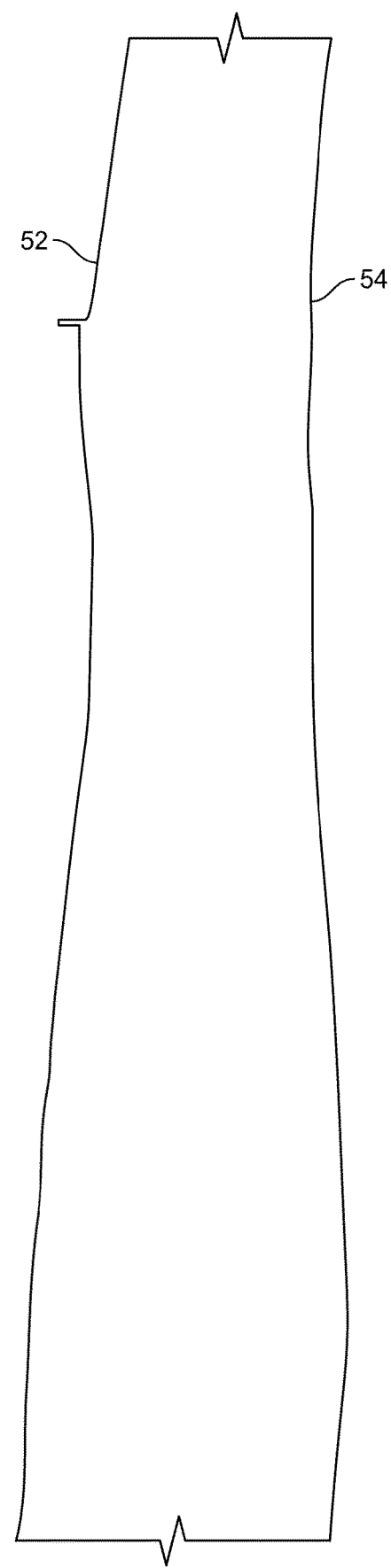
FIG. 15 shows a second embodiment of a knitting pattern with shaping at front and rear surfaces.

Alternatively, the knitting pattern may be shaped at both sides of the pattern. FIG. 15 shows a second embodiment of a knitting pattern having been shaped at both sides 52, 54 of the pattern. A garment produced by such a shaped knitting pattern may be more suited to patients who do not have a flat portion on a lower leg 12. For example, patients having oedema, obesity or lipoedema. Additionally, for stockings worn on an upper leg 12, shaping may be required. As such, a stocking may have a lower portion which is not shaped at one side, and an upper portion which is shaped at both sides.

Shaping at both sides may be conveniently provided by centre aligning the lines of the knitting profile. This provides symmetrically shaping for the garment.

However, for more accurate shaping, a plane may be defined across the associated representation 18. The plane extends through the interior of the representation 18, and is preferably normal to a front-to-back direction of the representation 18. The proportion of each representation course on one side of the plane may be recorded. The lines of the knitting profile may then be correspondingly aligned about a reference line. In other words, each line or knitting course of the knitting profile may have a proportion of the line or knitting course on one side of the reference line which corresponds to the proportion of the associated representation course which was on said side of the plane. As such, the knitting profile is shaped to correspond to the representation 18. The reference line may be considered to be internal to the knitting profile, rather than at an edge of the knitting profile.

The method further comprises a step S114 of knitting the compression garment based on the or each knitting pattern using the selected material. The bespoke compression garment may be knitted with a knitting machine.

The system may export quality information about the processing and quality checks for post-manufacture. Examples of this could include pressure maps, strain maps, transition markers, datapoints 10 or coordinates, measurements. The system could export key quality checks as a text file or spreadsheet for a knitting facility, with the knitting machine, to check against. The system may also generate the production documents with all the order information and the quality checks.

The system may be required to save or store all files, data, maps or other information generated. This could work in a variety of ways. For example, the system could store the files to a cloud location that is accessible by the knitting facility. A move advanced system could include a Graphical User Interface that has a process flow that integrates with an enterprise resource planning system. For example, the system could record the approval of quality checks by the operator and directly instruct the knitting machine. Other version of the system could integrate with an email system to notify the patient or clinician of the order progress.

Although a bespoke knitted compression garment is manufactured, it will be appreciated that this may not be necessary in all situations. For example, an off-the-shelf garment may be able to provide a sufficient pressure configuration to the patient. This may be the case if a geometry of the body part of the patient and a pressure therefor corresponds closely to that for which an off-the-shelf garment is designed. As such, once the scan or representation 18 and order information is provided to the system, the system may use a database of pre-existing compression garments having different size data and for applying different pressure configurations to determine whether an off-the-shelf garment may be suitable. A pre-existing compression garment from the database is selected based on matching or substantially matching size data and pressure configuration of the representation 18 to the size data and pressure configuration of the pre-existing compression garment. The pre-existing compression garment may then be ordered and provided to the patient. The clinician may utilise this option if a wait-time fora bespoke manufactured garment is unacceptable.

Although the compression garment is described as knitted, it will be appreciated that similar modelling methods and processes may be applied for non-knitted garments, for example woven garments or other garment construction.

Although the method describes generating a knitting profile and knitting the garment, it will be appreciated that these steps may be excluded if only a garment modelling process is required.

Although flat knit courses are described, it will be appreciated that helically knitted courses may be considered. Sections of the helical course may be modelled in a similar or identical way as the representation courses described above.

A system may be provided for manufacturing a bespoke knitted compression garment. The system comprises a body part scanner for scanning the body part of the patient and producing the representation, and pressure configuration data, in other words the pressure configuration prescribed by the clinician to be applied to the patient. The system further comprises material data, such as a database of characteristics of at least one material type. A processor or computer may be required to carry out the analysis steps on the representation and to produce the knitting pattern. A knitting machine may be required to knit the garment.

It is therefore possible to provide a method and system for providing a bespoke knitted compression garment which is accurately modelled on and represents a body part of a patient. By using the raw data from a scan to generate splines of best fit, which are used to calculate the number of needles for each course, courses of accurate circumference can be knitted which provides a pressure configuration to a patient which conforms to that which a clinician has prescribed.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. A method of making a bespoke knitted compression garment comprising material courses, the method comprising the steps of:
   a) providing a representation of a body part on which the compression garment is to be worn, the representation comprising a plurality of datapoints;
   b) determining a pressure configuration to be applied by the compression garment on the body part;
   c) defining a plurality of representation courses around the representation, each representation course representing one of the material courses of the compression garment when worn on the body part;
   d) selecting, for each representation course, a set of datapoints from the plurality of datapoints, each set of datapoints being located within one of the representation courses;
   e) fitting a curve to each set of datapoints;
   f) calculating a circumference value of each curve;
   g) determining a course pressure to be applied by each material course based on the pressure configuration;
   h) selecting a material for knitting at least part of the compression garment and determining a number of needles for each representation course based on the course pressure of the associated material course, a strain characteristic of the material, and the circumference value of the associated spline;
   i) producing a knitting pattern based on the number of needles for each representation course; and
   j) knitting the compression garment based on the or each knitting pattern using said material.

2. The method as claimed in claim 1, wherein said pressure configuration is non-uniform and at least two of the course pressures are different to each other.

3. The method as claimed in claim 1, wherein at least one representation course (32) is non-planar.

4. The method as claimed in claim 3, wherein, the non-planar representation course is defined as having at least two planar portions at an angle to each other.

5. The method as claimed in claim 4, wherein, during step e) said two planar portions of the non-planar representation course (32) are transformed so as to be coplanar.

6. The method as claimed in claim 3, wherein the representation courses each have at least one course height, the non-planar representation course having a non-uniform course height.

7. The method as claimed in claim 1, wherein the representation courses each have at least one course height, representation courses having a greater circumference value having a lower course height.

8. The method as claimed claim 1, further comprising the step k) after step e) and prior to step h) of defining a plurality of reference points around the circumference of each curve and determining a radius of curvature value of the curve (40) at each reference point, and during step h) the material and number of needles of each representation course is based on the radius of curvature of the reference points of the associated curve.

9. The method as claimed in claim 1, further comprising the step l) prior to step c) of analysing the representation to determine whether material courses of a lower leg of the garment when worn will be angularly offset relative to material courses of a foot of the garment when worn.

10. The method as claimed in claim 9, wherein during step l) said analysing comprises determining at least one transition point which characterises a transition between leg and foot, the transition point being determined by at least any one of: determining a point of maximum change in gradient of a curve defined by at least any one of forwardmost datapoints of the representation and rearwardmost datapoints of the representation; and determining the smallest distance on a forwardmost surface to a point which defines a back of a heel.

11. The method as claimed in claim 1, wherein the representation in step a) is provided with reference to a three-dimensional Cartesian coordinate system, said representation being a misoriented representation having an incorrect angle relative to a z-axis of said coordinate system, and further comprising a step n) after step a) wherein said misoriented representation is transformed to a representation having a correct orientation relative to said z-axis via rotating said misoriented representation by an angle defined between two markers having different z-axis positions, each marker being defined by an average x-axis or y-axis position of respective groups of datapoints of the misoriented representation having the same z-axis position.

12. The method as claimed in claim 1, wherein, during step i) said knitting pattern is smoothed to generate a smoothed knitting pattern to prevent or limit dropped stitches during step j).

13. The method as claimed in claim 1, wherein the knitting pattern is smoothed via adjusting the number of needles of the representation courses so that each knitting course of the smoothed knitting pattern has at least four adjacent knitting courses having an equal value of needles.

14. The method as claimed in claim 1, wherein knitting courses are aligned with respect to an internal line through the knitting pattern so that the garment when knitted is shaped at forwardmost and rearwardmost surfaces.

15. The method as claimed in claim 1, wherein the courses are flat knitted.

16. The method as claimed in claim 1, wherein the curve is at least any one of a spline and a convex hull, so that step e) comprises at least any one of: calculating a spline for each set of data points; and calculating a convex hull for each set of data points.

17. A knitted-compression-garment manufacturing system configured to perform the method as claimed in claim 1, comprising:
a body part scanner for providing a representation of a body part on which the compression garment is to be worn, the representation comprising a plurality of datapoints;
pressure configuration data representing a pressure to be applied by the compression garment on the body part;
material data including strain characteristics of at least one material;
a processor configured to
define a plurality of representation courses around the representation, each representation course representing one of the material courses of the compression garment when worn on the body part;
select, for each representation course, a set of datapoints from the plurality of datapoints, each set of datapoints being located within one of the representation courses;
fit a curve to each set of datapoints;
calculate a circumference value of each curve;
determine a course pressure to be applied by each material course based on the pressure configuration data;
select a material for knitting at least part of the compression garment and determining a number of needles for each representation course based on the course pressure of the associated material course, the material data, and the circumference value of the associated curve; and
produce a knitting pattern based on the number of needles for each representation course; and
a knitting machine for knitting the compression garment based on the or each knitting pattern using said material.

18. A compression garment made by the method as claimed in claim 1.

19. A method of modelling a bespoke knitted compression garment comprising material courses, the method comprising the steps of:
a) providing a representation of a body part on which the compression garment is to be worn, the representation comprising a plurality of datapoints;
b) defining a plurality of representation courses around the representation, each representation course representing one of the material courses of the compression garment when worn on the body part;
c) selecting, for each representation course, a set of datapoints from the plurality of datapoints, each set of datapoints being located within one of the representation courses;
d) fitting a curve to each set of datapoints; and
e) calculating a circumference value of each curve.

20. A method of providing a matched compression garment to a patient, comprising the steps of:
a) providing a representation of a body part of the patient on which the compression garment is to be worn, the representation comprising a plurality of datapoints and including size data corresponding to a size of the body part;
b) determining a pressure configuration to be applied by the compression garment on the body part;
c) providing a database of pre-existing compression garments having different size data and for applying different pressure configurations;
d) selecting a pre-existing compression garment from the database based on matching size data and pressure configuration of the representation to the size data and pressure configuration of the pre-existing compression garment; and
e) providing the pre-existing compression garment to the patient.

* * * * *